United States Patent [19]

Blom

[11] Patent Number: 5,507,809
[45] Date of Patent: Apr. 16, 1996

[54] MULTI-VALVED VOICE PROSTHESIS

[75] Inventor: Eric D. Blom, Indianapolis, Ind.

[73] Assignee: Hansa Medical Products, Inc., Indianapolis, Ind.

[21] Appl. No.: 148,655

[22] Filed: Nov. 5, 1993

[51] Int. Cl.$^6$ ............................................. A61F 2/20
[52] U.S. Cl. ............................................. 623/9; 623/11
[58] Field of Search ............................... 623/9, 11, 66; 604/167

[56] References Cited

U.S. PATENT DOCUMENTS

| | | | |
|---|---|---|---|
| 237,383 | 2/1881 | Halstead | 137/512 |
| 2,039,142 | 4/1936 | Brehm . | |
| 4,223,411 | 9/1980 | Schoendorfer et al. . | |
| 4,246,897 | 1/1981 | Muto . | |
| 4,291,690 | 9/1981 | Jessen . | |
| 4,325,366 | 4/1982 | Tabor . | |
| 4,435,853 | 3/1984 | Blom et al. . | |
| 4,538,607 | 9/1985 | Saul . | |
| 4,582,058 | 4/1986 | Depel et al. . | |
| 4,596,579 | 6/1986 | Pruitt . | |
| 4,614,516 | 9/1986 | Blom et al. . | |
| 4,623,348 | 11/1986 | Feit . | |
| 4,649,904 | 3/1987 | Krauter et al. | 604/167 |
| 4,653,660 | 3/1987 | Shaw . | |
| 4,655,752 | 4/1987 | Honkanen et al. | 604/167 |
| 4,695,275 | 9/1987 | Bruce et al. . | |
| 4,808,183 | 2/1989 | Panje . | |
| 4,911,716 | 3/1990 | Blom et al. | 623/9 |
| 4,964,850 | 10/1990 | Bouton et al. . | |
| 5,078,743 | 1/1992 | Mikalov et al. . | |
| 5,090,420 | 2/1992 | Nielsen . | |

FOREIGN PATENT DOCUMENTS

| | | |
|---|---|---|
| 0222509 | 5/1987 | European Pat. Off. . |
| 8024961 | 11/1980 | France . |
| 3121976A1 | 3/1982 | Germany . |
| WO88/02238 | 4/1988 | WIPO . |

*Primary Examiner*—Debra S. Brittingham
*Attorney, Agent, or Firm*—Barnes & Thornburg

[57] ABSTRACT

A voice prosthesis includes a cylindrical body for placement in an opening formed in the tracheoesophageal wall. The body has a first end lying on the esophageal side of the tracheoesophageal wall when the prosthesis is placed in the opening and a second end lying on the tracheal side of the tracheoesophageal wall. The body provides a passageway for airflow from its second end to its first end to provide alaryngeal speech-producing airflow from the esophagus. A first backflow-preventing valve controls the passageway to prevent the flow of fluids from the esophagus through the passageway to the trachea. A second backflow preventing valve is provided in series with the first backflow-preventing valve to prevent flow of fluids from the esophagus through the passageway to the trachea in the event of incompetence of the first backflow-preventing valve in the open or partially open orientation.

10 Claims, 1 Drawing Sheet

MULTI-VALVED VOICE PROSTHESIS

This invention relates to speech prostheses which permit the production of alaryngeal speech. It is disclosed in the context of a particular type of such a voice prosthesis. However, it is believed to be useful with other types of voice prostheses as well.

Several different types of voice prostheses useful for the production of alaryngeal speech are known. There are, for example, the prostheses described in U.S. Pat. Nos. 4,911,716; 4,614,516; and, 4,435,853, and numerous references cited in those patents. The trend toward increasing the dwelling time of such prostheses in the tracheoesophageal wall of a wearer has been noted in, for example, U.S. Pat. No. 4,911,716. The reasons for increasing the dwelling time include the difficulty that some wearers have in inserting and removing the prostheses and the tendency of the puncture in the tracheoesophageal wall to close when the prosthesis is removed from it. This tendency sometimes even necessitates reforming the puncture.

Voice prosthesis devices of these types are generally constructed from relatively soft, pliable biocompatible materials. Certain species of Candida, fungus that occasionally infects mucus membranes of the throat and trachea can grow on the voice prostheses and distort the valves incorporated in the voice protheses. See, Mahieu, H. F., et al., "Candida Vegetations on Silicone Voice Prostheses, "Arch. Otolaryngol, Head Neck Surg., March 1986, Vol. 112, pp. 321–325. Such distortion sometimes renders the valves incapable of closing. Consequently, it is not uncommon for a wearer of a voice prosthesis device of these general types to have to remove the device, for cleaning or for replacement.

In such users, it is not uncommon for the device to be out of the user's fistula for a period of up to five to ten minutes during which time either an alternative prosthesis is put in its place or a catheter is put in to maintain the fistula. If the user fails to maintain the fistula at all times, it will close rapidly, even in as short a time as five to ten minutes, to the point that the patient cannot get the device back into the fistula. This requires that another surgical operation be performed to reopen the fistula so that the cleaned voice prosthesis device or a new voice prosthesis device can be inserted. Some surgeons have expressed a reluctance to use voice prosthesis devices of these general types because of this propensity of the fistula to reclose when the voice prosthesis device is removed for regular hygiene, repair or replacement.

Additionally, many patients have found that it is sometimes difficult to replace the voice prosthesis device in the fistula even when the voice prosthesis device is only out for a relatively shorter period of time than that necessary for the fistula to close completely. The fistula prolapses essentially immediately when the voice prosthesis device is removed, and so is somewhat smaller even when the device has not been out of the fistula for too long a period of time.

One prior art solution to the defective valve problem is to provide a plug which the wearer can insert into the tracheal end of his prosthesis through his tracheostoma. The plug is on a retaining strap which extends around the neck of the wearer to reduce the danger of the plug being dislodged from the end of the prosthesis and aspirated. This solves the problem of aspiration of fluids through the prosthesis in the case of an incompetent open or partially open valve. However, it does not restore speech.

It is an object of the invention to provide an apparatus for permitting alaryngeal speech-generating capability in the case of a wearer whose prosthesis device has a one-way valve that becomes incompetent in the open or partially open position.

According to the invention, a voice prosthesis includes a cylindrical body for placement in an opening formed in the tracheoesophageal wall. The body has a first end lying on the esophageal side of the tracheoesophageal wall when the prosthesis is placed in the opening and a second end lying on the tracheal side of the tracheoesophageal wall when the prosthesis is placed in the opening. The body provides a passageway for airflow from its second end to its first end to provide alaryngeal speech-producing airflow from the esophagus, and a first backflow-preventing valve controlling the passageway to prevent the flow of fluids from the esophagus through the passageway to the trachea. A second backflow preventing valve is provided in series with the first backflow-preventing valve to prevent flow of fluids from the esophagus through the passageway to the trachea in the event of failure of the first backflow-preventing valve.

Illustratively, according to the invention, the first backflow-preventing valve is provided adjacent the first end of the body.

Further illustratively according to the invention, the second backflow-preventing valve is provided between the first backflow preventing valve and the second end of the body.

Additionally, illustratively, the second backflow-preventing valve is removably provided between the first backflow preventing valve and the second end of the body.

Further illustratively the first valve comprises a first valve seat provided in the passageway, and a first valve flap provided adjacent the first valve seat and formed to move away from the first valve seat toward the first end of the body when a pressure differential is developed across the first valve seat with the second end of the body at a positive pressure relative to the first end of the body.

Additionally, illustratively, the second valve comprises a second valve seat provided in the passageway, and a second valve flap provided adjacent the second valve seat and formed to move away from the second valve seat toward the first end of the body when a pressure differential is developed across the second valve seat with the second end of the body at a positive pressure relative to the first end of the body.

Alternatively, the second valve comprises a second valve seat for selectively removable coupling to the second end of the body, and a second valve flap provided adjacent the second valve seat and formed to move away from the second valve seat toward the first end of the body when the second valve is coupled to the passageway upstream from the first end and a pressure differential is developed across the second valve seat with the second valve flap side of the second valve seat at a negative pressure relative to the other side of the second valve seat.

The invention may best be understood by referring to the following description and accompanying drawings which illustrate the invention.

Figure 1:
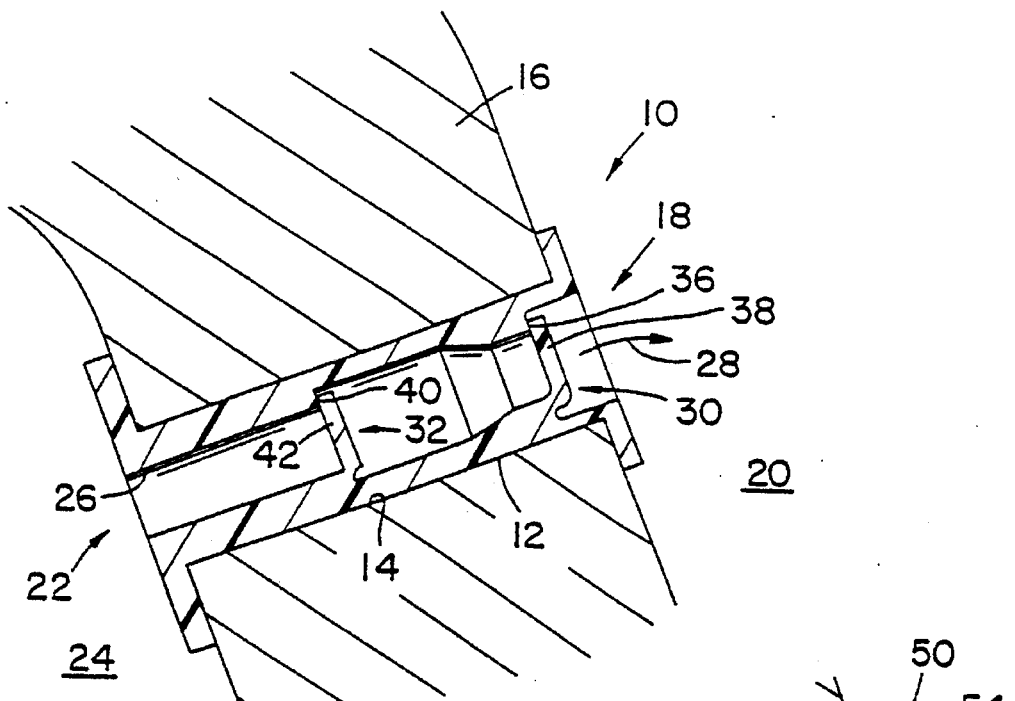
FIG. 1 illustrates a fragmentary longitudinal sectional view taken through the trachea, esophagus and tracheoesophageal wall of a wearer of a voice prosthesis device constructed according to the invention.

Referring now to FIG. 1, a voice prosthesis 10 includes a cylindrical body 12 for placement in an opening 14 formed in the tracheoesophageal wall 16. The body 12 has a first end 18 lying on the esophageal side 20 of the tracheoesophageal wall 16 when the prosthesis 10 is placed in the opening 14 and a second end 22 lying on the tracheal side 24 of the tracheoesophageal wall 16 when the prosthesis 10 is placed in the opening 14. The body 12 provides a passageway 26 for airflow from its second end 22 to its first end 18 to provide alaryngeal speech-producing airflow 28 from the esophagus 20. A first backflow-preventing valve 30 controls the passageway 26 to prevent the flow of fluids from the esophagus 20 through the passageway 26 to the trachea 24. A second backflow preventing valve 32 is provided in series with the first backflow-preventing valve 30 to prevent flow of fluids from the esophagus 20 through the passageway 26 to the trachea 14 in the event of failure of the first backflow-preventing valve 30 in the open or partially open orientation. The first backflow-preventing valve 30 is provided adjacent the first end 18 of the body 12. The second backflow-preventing valve 32 is provided between the first backflow preventing valve 30 and the second end 22 of the body 12. The first valve 30 comprises a first valve seat 36 provided in the passageway 26, and a first valve flap 38 provided adjacent the first valve seat 36 and formed to move away from the first valve seat 36 toward the first end 18 of the body 12 when a pressure differential is developed across the first valve seat 36 with the second end 22 of the body 12 at a positive pressure relative to the first end 18 of the body 12. The second valve 32 comprises a second valve seat 40 provided in the passageway 26 and a second valve flap 42 provided adjacent the second valve seat 40 and formed to move away from the second valve seat 40 toward the first end 18 of the body 12 when a pressure differential is developed across the second valve seat 40 with the second end 22 of the body 12 at a positive pressure relative to the first end 18 of the body 12.

Figure 2:
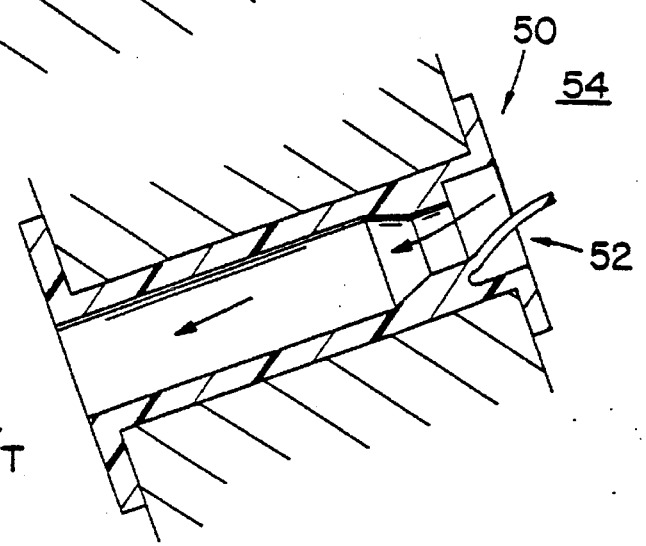
FIG. 2 illustrates a fragmentary longitudinal sectional view taken through the trachea, esophagus and tracheoesophageal wall of a wearer of a prior art voice prosthesis device, the one-way valve of which has become incompetent in the open or partially open orientation; and, FIG. 3 illustrates the device of FIG. 2 with a device according to the invention inserted into the tracheal end thereof.
Figure 3:
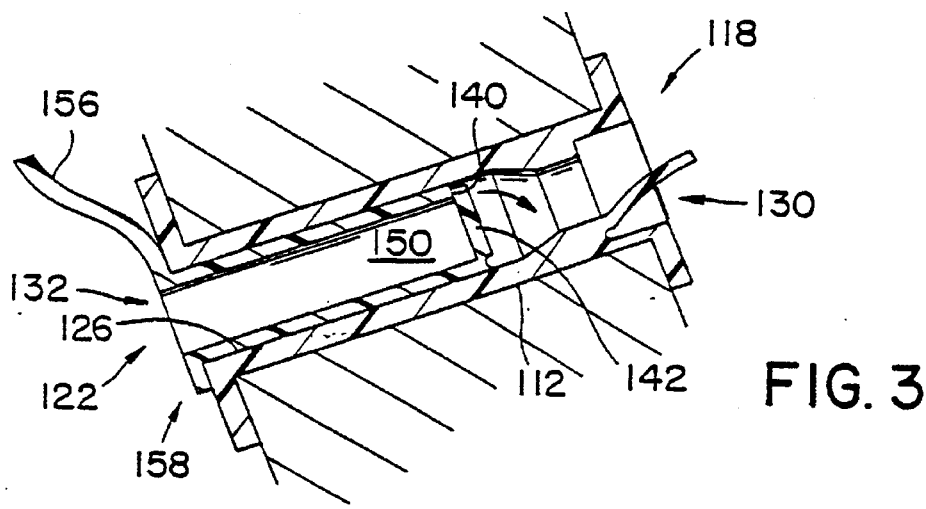

FIG. 2 illustrates a prior art voice prosthesis 50 in which the one-way valve 52 has become incompetent in the open or partially open position. The wearer is not protected from the flow of material backward through valve 52. A prosthesis of the type illustrated in FIG. 1 solves this problem by putting a second one-way valve 32 in series with the first one-way valve. Another solution to the problem of an incompetent open or partially open one-way valve 52 in a prior art prosthesis 50 is illustrated in FIG. 3 In FIG. 3, a second backflow-preventing valve 132 is removably provided between the first backflow preventing valve 130 and the second end 122 of the body 112. The second valve 132 comprises a second valve seat 140 for selectively removable coupling to the second end 122 of the body 112, and a second valve flap 142 provided adjacent the second valve seat 140 and formed to move away from the second valve seat 140 toward the first end 118 of the body 112 when the second valve 132 is coupled to the passageway 126 upstream from the first end 118 and a pressure differential is developed across the second valve seat 140 with a second valve flap 142 side of the second valve seat 140 at a negative pressure relative to the other side 150 of the second valve seat 140. A strap 156 is provided on the plug 158 providing second valve seat 140 and second valve flap 142. If the valve 130 should become incompetent in the open or partially open orientation, the wearer need only insert plug 158 containing second valve 132 through his tracheostoma into passageway 126. Strap 156 can be secured on the outside of the wearer's tracheostoma to reduce the likelihood of aspiration of plug 158 and its components in the event plug 158 becomes dislodged from passageway 126.

It is also believed that placement of a second one-way valve closer to the tracheal end of the prosthesis will reduce the ingress into the tracheal end of the prosthesis of the phlegm which wearers clear from their airways several times a day.

What is claimed is:

1. In a voice prosthesis of the type including a cylindrical body for placement in an opening formed in the tracheoesophageal wall, said body having a first end lying on an esophageal side of said tracheoesophageal wall when said prosthesis is placed in said opening and a second end lying on a tracheal side of said tracheoesophageal wall when said prosthesis is placed in said opening, said body providing a passageway for airflow from said second end to said first end to provide alaryngeal speech-producing airflow from said esophagus, and a first backflow-preventing valve controlling said passageway to prevent flow of fluids from said esophagus through said passageway to said trachea, the improvement comprising a second backflow preventing valve in series with said first backflow-preventing valve to prevent flow of fluids from said esophagus through said passageway to said trachea in the event of failure of said first backflow-preventing valve.

2. The apparatus of claim 1 wherein said first backflow-preventing valve is provided adjacent said first end of the body.

3. The apparatus of claim 1 or 2 wherein said second backflow-preventing valve is provided between said first backflow preventing valve and said second end of said body.

4. The apparatus of claim 3 wherein said second backflow-preventing valve is removably provided between said first backflow preventing valve and said second end of said body.

5. The apparatus of claim 1 or 2 wherein said first valve comprises a first valve seat provided said passageway, and a first valve flap provided adjacent said first valve seat and formed to move away from said first valve seat toward said first end of said body when a pressure differential is developed across said first valve seat with said second end of said body at a positive pressure relative to said first end of said body.

6. The apparatus of claim 5 wherein said second valve comprises a second valve seat provided in said passageway, and a second valve flap provided adjacent said second valve seat and formed to move away from said second valve seat toward said first end of said body when a pressure differential is developed across said second valve seat with said second end of said body at a positive pressure relative to said first end of said body.

7. The apparatus of claim 3 wherein said first valve comprises a first valve seat provided in said passageway, and a first valve flap provided adjacent said first valve seat and formed to move away from said first valve seat toward said first end of said body when a pressure differential is developed across said first valve seat with said second end of said body at a positive pressure relative to said first end of said body.

8. The apparatus of claim 7 wherein said second valve comprises a second valve seat provided in said passageway, and a second valve flap provided adjacent said second valve seat and formed to move away from said second valve seat toward said first end of said body when a pressure differential is developed across said second valve seat with said second end of said body at a positive pressure relative to said first end of said body.

9. The apparatus of claim 4 wherein said first valve comprises a first valve seat provided in said passageway, and a first valve flap provided adjacent said first valve seat and formed to move away from said first valve seat toward said first end of said body when a pressure differential is developed across said first valve seat with said second end of said body at a positive pressure relative to said first end of said body.

10. The apparatus of claim 9 wherein said second valve comprises a second valve seat for selectively removable coupling to said second end of said body, and a second valve flap provided adjacent said second valve seat and formed to move away from said second valve seat toward said first end of said body when said second valve is coupled to said passageway upstream from said first end and a pressure differential is developed across said second valve seat with said second valve flap side of said second valve seat at a negative pressure relative to another side of said second valve seat.

* * * * *